United States Patent
Mathur et al.

(10) Patent No.: US 6,368,860 B1
(45) Date of Patent: Apr. 9, 2002

(54) ANTHOCYANIN PRODUCING CALLUS LINE IN CULTURES OF PANAX SIKKIMENSIS AND A METHOD OF PRODUCING PANAX SIKKIMENSIS LINE CAPABLE OF PRODUCING ANTHOCYANIN

(75) Inventors: Archana Mathur; Anita Gangwar; Ajay Kumar Mathur; Rajender Singh Sangwan; Dharam Chand Jain, all of Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/538,425

(22) Filed: Mar. 29, 2000

(51) Int. Cl.[7] .................................................. C12N 5/00
(52) U.S. Cl. ...................... 435/420; 435/430; 435/430.1
(58) Field of Search ................................ 435/420, 430, 435/430.1

(56) References Cited

U.S. PATENT DOCUMENTS 5,716,848 A * 2/1998 Dalsgard et al.
6,140,121 A * 10/2000 Ellington et al.

* cited by examiner

Primary Examiner—Leon B. Lankford, Jr.
(74) Attorney, Agent, or Firm—Weingarten, Schurgin, Gagnebin & Lebovici LLP

(57) ABSTRACT

The present invention relates to an anthocyanin producing callus line in cultures of Panax sikkimensis (an Indian species of ginseng) said line comprising: (a) Characteristic pink-purple pigmentation, (b) Growth index of about 221–450 in about 50–80 days of culture period, (c) Yield of anthocyanin (2–3 mg/gf.wt.) from the callus in about 40–60 days under light conditions (continuous light), and (d) Characteristic DNA profile wherein the lanes 1,2,3,4,5,6,7,8,9,10,11 and 12 in each gel (upper gel for wild line and lower gel for anthocyanin producing line) represent the PCR amplified fragments produced by the respective template megabase genomic DNA with primers 5' CTG ATG CAT C3', 3',5' TGG TCA CTG A 3', 5' AGG GGT CTT G 3',5' GAA ACG GGT G 3',5' AGG GGT CTT G 3',5' GCG TAA CGC C 3',5' CAG CAC CCA C 3',5' GTT GCG ATC C 3',5' CAG GCC CTT C 3',5' CGC AGT ACT C 3',5' GTC CTA CTC G 3',5' CTA CAC AGG C 3' and 5' GTC CTT AGC G 3', respectively. Lane M shows the standard size markers of a ladder at 100 bp intervals from 1000 bp downwards.

16 Claims, 1 Drawing Sheet

US 6,368,860 B1

Figure 1:
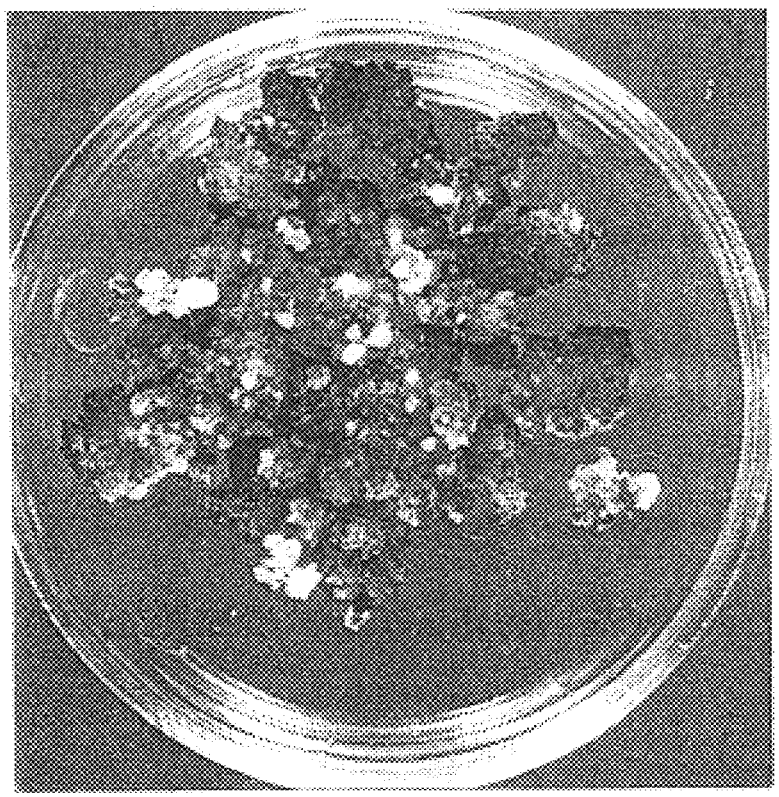

ANTHOCYANIN PRODUCING CALLUS LINE IN CULTURES OF PANAX SIKKIMENSIS AND A METHOD OF PRODUCING PANAX SIKKIMENSIS LINE CAPABLE OF PRODUCING ANTHOCYANIN

FIELD OF THE INVENTION

The present invention relates to a novel process for the development of an anthocyanin producing callus line in cultures of *Panax sikkimensis*-Indian Ginseng. More particularly, the developed callus line has characteristic pigmentation, growth kinetics, DNA profile and anthocyanin content.

1. Background

The invention provides a procedure for the development of an anthocyanin producing callus line in cultures of *Panax sikkimensis*-Indian Ginseng, its growth kinetics and in vitro productivity of anthocyanin in this unique line which also contains ginsenosides that are in high demand in market as important ingredient of health tonics and anti-ageing drug preparation.

The genus Panax (Family Araliaceae) which is commonly called ginseng, has long been known for its saponin (ginsenosides) responsible for anti-ageing, adaptogenic and immunomodulatory activity. We have been engaged in biotechnological studies in American and Indian species of Panax for past several years. While screening cell lines specifically rich in various ginsenoside fractions, from callus cultures of an Indian species—*P. sikkimensis*. we came across with anthocyanin rich cell clusters which have subsequently been cloned through continuous cell-aggregate selection procedure.

2. Prior Art References

Anthocyanins are widely formed in various plant species and are most conspicuous in flower and fruit parts. Because of their low toxicity, anthocyanins have a high potential as a food additive and marker. Therefore, many institutes and food manufacturers are engaged in intensive research to produce these pigments from various plant cell cultures such as *Euphorbia milli* (Agri.Biol.Chem.53:417–423, 1989); *Callistephus chinensis* (Pl.Cell Rep.5:435–438,1986); *Vitis vinifera* (Biotech.Agri.Forest.Vol.24,Med. Pl. V,ed.Y. P. S.Bajaj,pp 373–386,1993); Srawbeny (J.Sci.Food Agric.66:381–388,1994); *Perilla frutescens* (J.Ferment. Bioeng. 76: 530–531,1993); Aralia cordata (Pl. Cell Tiss. Org. Cul. 36: 21–26,1994) etc. Anthocyanins, however, usually accumulate only in small amounts in cultured plant cells and their production generally requires light irradiation. One of the highest reports of anthocyanin production has been in Glehnia littoralis (Phytochemistry 48: 279–282, 1998) callus cultures where as high as 14.2% $g^{-1}$ D.Wt. anthocyanin production has been obtained. In many cases, anthocyanins produced in vitro are of cyanidin type which are biochemically more primitive than those of the original plant where methylated antrhocyanidins are present (Rev. Can. Biol. Exp.42:13–18, 1983). Seven different anthocyanidins were detected:cyanidine (17 spp.), delphinidin (5 spp.) malvinidine (4 spp.) petunidin (3 spp.), pelargonidin (2 spp.) and one example for both peonidin and hirsutidin.

Although in vitro anthocyanin production has been reported in many other genera mostly in callus/suspension cultures (Phytochemistry 29: 2153–2158,1990, Biotechnol. Agric. Forest. Vol. 24; Ed. Bajaj pp 373–386, 1993), to the best of our knowledge there has been no report of its production in the genus Panax Panax is probably the sole source of an important group of secondary metabolites namely ginsenosides which are used as adaptogens. The root extract/powder of this important plant is marketed in the form of tonics, teas, chewing gums, face creams (for rejuvenating skin) etc. Occurrence of anthocyanin in the same callus along with ginsenosides will further add to its market potential. The coloured extract with ginsenosides can be used in candy's, cakes, pastries, cold drinks etc.

OBJECTS OF THE INVENTION

The main object of the present invention is to devise a procedure for the development of an anthocyanin producing callus line in cultures of Indian ginseng *Panax sikkimensis* with characteristic pigmentation, growth kinetics, DNA profile and anthocyanin content. To the best of our knowledge so far, nobody has reported occurrence of anthocyanin in callus cultures of any Panax species especially *P. sikkimensis*.

Another object of the present invention is to provide a novel *P. sikkimensis* callus line capable of producing high quantity of anthocyanin Yet another object of the present invention is to study the growth kinetics in relation to anthocyanin production in callus cultures of *P. sikkimensis*.

Still another object of the present inventions is to extract ginsenosides from anthocyanmin producing callus line.

Still another object of the present invention is to identify the physical conditions for increased anthocyanin production.

Still another object of the present invention is to characterise the anthocyanin producing line at the molecular level.

Still another object of the present invention is to characterize the anthocyanin pigment. Still another object of the present invention is simultaneous recovery of anthocyanin and ginsenoside.

DETAILED DESCRIPTION OF THE INVENTION

To meet the above objects and others, the present invention provides a novel *Panax sikkimensis* (an Indian species of ginseng) callus line which produces anthocyanin, said line comprising:

(a) Characteristic pink-purple pigmentation, (b) Growth index of about 221–450 in about 50–80 days of culture period, (c) Yield of anthocyanin (2–3 mg/gf.wt.) from the callus in about 40–60 days under light conditions (continuous light), and (d) Characteristic DNA profile wherein the lanes 1,2,3,4, 5,6,7,8,9,10,11 and 12 in each gel (upper gel for wild line and lower gel for anthocyanin producing line) represent the PCR amplified fragments produced by the respective template megabase genomic DNA with primers 5' CTG ATG CAT C, 3',5' TGG TCA CTG A 3', 5' AGG GGT CTT G 3',5' GAA ACG GGT G 3',5' AGG GGT CTT G 3', 5' GCG TAA CGC C 3',5' CAG CAC CCA C 3',5' GTT GCG ATC C 3', 5' CAG GCC CTT C 3',5' CGC AGT ACT C 3',5' GTC CTA CTC G 3',5' CTA CAC AGG C 3' and 5' GTC CTT AGC G 3', respectively. Lane M shows the standard size markers of a ladder at 100 bp intervals from 1000 bp downwards.

The present invention also provides a method for the development of an anthocyanin producing line of *P. sikkimensis* from root explants wherein the said method comprising the steps of:

(a) establishment of aseptic cultures of root explants of *P. sikkimensis* on modified Murashige and Skoogs medium (Medium I) to obtain callus, (b) transferring the primary calli to medium II for optimal growth along with anthocyanin production, (c) maintaining and multiplying the callus for over 3 years by regular subculturing in medium II at every 4–6 weeks under dark and/or light cycle, temperature 28±3° C., 70–80% relative humidity, (d) isolating the anthocyanin producing callus line by selectively subculturing the cell culture which exhibited the presence of anthocyanin for atleast 5–8 subsequent subcultures, and (e) proliferating the enriched callus line by using medium II and incubating the callus cultures under specified light conditions (16 hrs. light/8 hrs. dark or 24 hrs. light).

THE NOVELTIES OF THE INVENTION ARE AS FOLLOWS a) To the best of our knowledge, the present invention reports for the first time a procedure for the development of anthocyanin producing callus line in *P. sikkimensis* with appreciably high anthocyanin content (2.16% F. Wt.) in addition to the characteristic ginsenosides (0.9–1.2% F. Wt). The procedure outlines the protocol for induction of callus from excised root pieces of *P. sikkimensis*. a callus culture multiplication and maintenance medium (nutrient+growth supplements) and incubation environment (physical conditions) that support sustained growth and anthocyanin production over more than 3 years tested so far.

b) The invention has resulted in obtaining the pigment anthocyanin as well as ginsenosides from the same callus tissue.

c) The invention has resulted in bench level identification of parameters such as light conditions (light-dark cycle, continuous light and complete darkness) and harvesting schedule, hormone concentration and specification etc. for anthocyanin production.

d) The developed line has a morphologically distinguishable feature, the accompanying photograph, (sheet 1, FIG. 1) depict the characteristic dark pink purple pigmentation in the callus cells of the isolated line in comparison to the wild counterpart. The morphological appearance is as nearly true as is reasonably possible to make the same in colored illustration of this character and e) The developed line has characteristic DNA profile (Sheet 1, FIG. 2).

In a preferred embodiment of the process the roots are cut into 4–7 mm small explants; are sterilized by treatment with 1% cetabelon (v/v) for a period of about 5–15 minutes, then with 70% (V/v) ethanol for 30 sec., followed by treatment with 0.1% $HgCl_2$ (w/v) for about 1–2 min. The basal medium in step (a) is modified Murashige and Skoog's (1962) medium supplemented with 200 mg/l myoinositol, 10 mg/l each of thiamine hydrochloride and pyridoxine hydrochloride and 5 mg/l of nicotinic acid (Medium I), and medium II used in step (b) is obtained by addition of 2,4-dichlorophenoxyacetic acid (0.1–2.0 mg/l) and Kn (0.1–0.5 mg/l), that are preferably added to the basal medium for optimal callus growth.

BRIEF DESCRIPTION OF THE ACCOMPANYING DRAWINGS

FIG. 1. is a photograph that shows the developed callus line of *P. sikkimensis* of the said invention.

Figure 2:
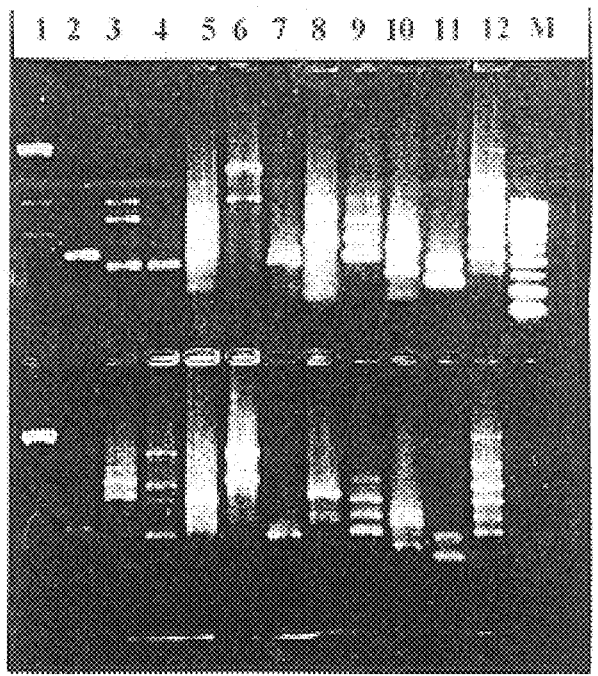

FIG. 2. is a photograph that represents the DNA profile of the developed callus line of *P. sikkimensis*.

Accordingly, the present invention provides a procedure for the development of an anthocyanin producing callus line of *P. sikkimensis* root explants having (a) characteristic pigmentation (sheet 1, FIG. 1). In addition to the anthocyanin, the said callus line also contains 0.9–1.2% F. Wt. of crude ginsenoside. (b) having crude ginsenoside (0.9–1.2%) characteristic of the genus Panax, (c) DNA profile as shown in FIG. 2, (c) high growth index (221.36–433.172) resulting in more biomass production and high anthocyanin content (upto 2.5 mg/g.f.wt) under specific light conditions (8 hrs light and 16 hrs dark; 16 hrs light/8 hrs dark; 24 hrs light and 24 hrs dark) and particular lhormone combination and concentration, IAA (0.5–1.5 mg/l); NAA (0.5–1.5 mg/l); all in combination with Kn (025–0.50 mg/l) (d) specific absorption spectra of the anthocyanin pigment having Rf (0.404).

The invention further provides the process which comprises establishment of aseptic callus cultures from root explants of *P. sikkimensis* on modified Murashige & Skoog's medium (Physiol. Plant, 15:473–497, 1962) supplemented with 2,4-D (0.0–5.0 mg/l) or NAA (0.1–2.0 mg/l), either alone or in combination with Kn (0.1–2 mg/l), the calli were maintained by periodic transfer to fresh medium in the dark and/or light cycle, then isolating anthocyanin producing cell line by selectively subculturing the cell cluster which usually contained anthocyanin pigment, repeating the selection procedure every 3–4 weeks under similar conditions, finally cloning the anthocyanin producing cell line, for growth measurements under static conditions, inoculum to medium ratio was 1:10, harvesting done at 10 days interval, biomass increase was expressed as percent increment over the initial inoculum, dried and samples to constant weight in a hot air oven at 80° C. to measure dry matter content.

In yet another embodiment of the present invention, chemical extraction of ginsenosides from freshly harvested callus, was done with methanol (100%, 4 times), redissolving the dried extract in water and finally extracting this water portion with n-butanol saturated with water (4 time), collecting the n-butanol fraction, centrifuging it and collecting the supernatant, drying it under vacuum.

In yet another embodiment the anthocyanin pigment was extracted from fresh callus tissue by homogenising it in 0.1% (v/v) HCl-methanol (10 ml), filtering it, diluting the supernatent 3 folds with acidic methanol solution, measuring its absorbance at wavelengths ranging from 525–535 nm using UV/VIS spectro photometer (Perkin Elmer, Lambola Bio 23).

In yet another embodiment the presence of anthocyanin in the cells of the selected line was confirmed by the non radiative resonance energy transfer (RET) procedure (PI. Med. 60:253–259, 1994) using 0.2 mg/l fluoroscein isothiocyanate (FITC) staining.

In yet another embodiment of the present invention, the development anthocyanin producing line is characterized at the molecular level using cell line genomic DNA as template in the randomly primed polymerase chain reaction (RP-PCR) assays.

In yet another embodiment of the present invention, the cultural conditions-light (8 hrs light and 16 hrs dark; 16 hrs light/8 hrs dark; 24 hrs light and 24 hrs dark) and particular hormone combination and concentration, [IAA (0.5–1.5 mg/l); NAA (0.5–1.5 mg/l); 2,4-D (0,5–1.5 mg/l); all in combination with Kn (0.25–0.50 mg/l)] as well as light dark conditions were determined to maximize anthocyanin production.

In yet another embodiment of the present invention a procedure to isolate different fractions of the pigment and separating the major fraction of the anthocyanin pigment was performed using paper chromatography using the solvent system, n-Butanol: acetic acid: water (BAW)::(4:1:5), organic layer (upper layer) and the Rf value of the various distinct fractions of the anthocyanin pigment were determined for their identification.

The following description is provided for illustration only and this should not be construed to limit the scope of the invention in any manner.

BRIEF METHODOLOGY OF THE PRESENT INVENTION INCLUDES

(a) Establishment of Aseptic Callus Cultures

*P sikkimensis* Ban. (Indian Forester 109: 840–847) calli were obtained from root pieces collected from Lachung area of Sikkim, India (1500–3000 m, altitude) (Pl. Med. 65:484–486). The explants (3–5 mm) were thoroughly washed to remove soil particles. They were then treated with 1% cetavelon (v/v) solution and thereafter surface sterilized with 70% (v/v) ethanol for 30 sec., followed by treatment with 0.1% $HgCl_2$; (w/v) solution for 2 minutes. After surface sterilization the explants were implanted onto the agar-gelled medium fortified with various combinations of hormones. The basal medium used in the present study was devised by incorporating inorganic salts of Murashige and Skoog's [Physiol. Plant. 15: 473–497 (1962)] medium, 3% sucrose, 200 $mgl^{-1}$ myoinositol, 10 $mgl^{-1}$ each of thiamine hydrochloride (THCl) and pyridoxine hydrochloride (PHCl) and 5 $mgl^{-1}$ nicotinic acid. The pH of the medium combinations were adjusted to 5.8±0.03 before autoclaving at 1.04 $kg/cm^2$ pressure (121° C.) for 15–20 minutes. The cultures were incubated at 25±3° C. in diffused light (unless otherwise stated) at 60–70% relative humidity. The calli were maintained by periodic transfer to fresh medium in the dark and/or light cycle. Anthocyanin producing cell line was isolated by selectively subculturing the cell cluster which usually contains anthocyanin pigment. The selection procedure was carried out every 3–4 weeks under similar conditions. After cloning, anthocyanin producing cell line was subcultured every 3–4 weeks.

(b) Growth Kinetic Studies of the Anthocyanin Producing Line

For growth measurement under static conditions, 3 gm fresh weight of callus was inoculated onto 30 ml of the fresh medium and the tissue was harvested at 7 days interval. The fresh weight of the cultured tissue was measured by carefully removing the adhered agar from callus cultures. The biomass increase on a fresh weight basis is expressed as the percent increment over the initial inoculum. The samples were dried to constant weight in a hot air oven at 80° C. to measure the dry matter content. A minimum of 3 replicates were used for all the growth assay treatments and the experiments were repeated twice. The data are expressed as the mean performance of all the replicates in terms of their growth index (GI).

(c) Molecular Characterization of the Developed Anthocyanin Producing Line

The developed line as well as the wild line were genetically characterized through molecular marker patterns generated using their genomic DNAs as template in the randomly primed polymerase chain reaction (RP-PCR) assays. The amplification reaction mixture, in a final volume of 25 $\mu$l, contained 400 $\mu$M each dNTP, 1.0 mM MgCIa, 10 pmoles of primer, 0.25 units of Taq polymerase and 2.5 $\mu$l Taq buffer (Bangalore Genei, India), 50 ng template DNA. After a single pre-PCR cycle of 94° C. (5 min), 35° C. (1.5 min), and 10° C. (15 min), the reaction mixture contents were cycled to 40 times with each cycle consisting of a sequence of 94° C. (1.5 min), 35° C. (1.5 min) and 72° C. (1.0 min) and were finally given an extension completion incubation of 72° C. for 5 min in a PCR machine (Perkin Elmer Model 2400). At the end of PCR run, the amplification products were separated electrophoretically on a 1.4% agarose in I×TAE buffer. A mixture of 1000–100 base pairs (bp) of ladder of 10 double stranded (ds) DNA fragments were coelectrophoressed to guage the size (bp) of the amplification products.

(d) Extraction and TLC Analysis of Crud Ginsenosides

The extraction of crude ginsenosides from the callus tissue was done according to the procedure reported earlier by us (Phytochem. 35: 1221–1224; Planta Med. 65:484–486,1999). Briefly, a known amount of fresh callus tissue was extracted overnight with MeOH and the procedure was repeated four times. The pooled methanolic extract was conentrated and dried at 60° C. The residue was redissolved in 10 ml water and extracted with $Et_2O$ at room temperature. The water fraction was collected and extracted with n-BuOH satyrated with water. The BuOH fraction was finally concentrated under reduced pressure and weighed to get crude ginsenoside content. The crude ginsenosides obtained above were further resolved into different fraction by TLC. For this the crude mixture was spotted onto 60F/254 E.Merck precoated plates along with known amounts of standard ginsenosides (Rb1, Rb2, Re, Rd, Re, Rf, Rgl; Carl Roth, Germany). $CHCl_3:MeOH:H_2O$ (13:7:2, lower phase) gave the best separation and resolution. Detection of spots was accomplished by spraying the plates with 10% (v/v) $H_2SO_4$.

(e) Extraction of Anthocyanin Pigment

Callus tissue was homogenised in 0.1% (v/v) HCl-methanol (10 ml). After filtration, 1ml of the clear supematent was diluted 3-fold with the same acidic methanol solution. The absorbance of the methanolic solution was measured at 535 nm using a uv/vis spectrophotometer (Perkin Elms Lambola Bio 23). The anthocyanin content was estimated and anthocyanin yield was calculated following. Sakamoto et al. (1994) (Pl.Cell Tiss. Org. Cult. 36:21–26).The total anthocyanin concentration of the extract solution is determined using the extrinction coefficient E 1%≡98.2 at 535 nm for cranberry anthocyanin extracted with the same solvent (Pl. Cell Tiss. Org. Cult. 36: 21–26, 1994).

$$\text{Anthocyanin content } (\mu g) = \frac{1 \times A_{535} \times 10{,}000 \times \text{Volume (ml)}}{98.2}$$

Paper Chromatography of Anthocyanins

Freshly harvested plant tissue was extracted with 0.1% Hcl—MeOH (three times). The total extract is concentrated under vacuum at 40–50° C. and the concentrate applied directly on to the whatman filter paper No. 3 is run into descending order in the solvent system Butanol: acetic acid: water:: 4:1:5 organic layer at room temperature. The paper is run for 10–15 hrs. The anthocyanins appear as clear discrete coloured bands which are then cut out from the dried papers and pigments eluted with methanol. The eluates are collected and concentrated, the process is repeated atleast three times. The two bands were separated on paper in above solvent system having Rf values 0.40 and 0.73, respectively.

Spectral properties: Anthocyanins in acid solutions have two main absorption maxima, one in visible region between 470–550 nm and a smaller one in the UV at about 270–280 nm. The position of visible and UV peaks in 0.1% Hcl—MeOH solvent is recorded as FIG. 3. The band having Rf 0.40 is the major one having and has maximum absorption at 528.99 nm and the one showing Rf 0.73 has maximum absorption at 536.51 nm.

The following examples are given by way of illustration of the present invention and should not be to construed to limit the scope of the present invention.

EXAMPLE 1

Biomass production as well as anthocyanin content under different hormone concentrations and combinations were compared over a culture span of 80 days. Growth Index and anthocyanin content were monitored at 10 days interval and the results are depicted in Table 1. The table clearly indicates that NAA (0.5)+Kn (0.25) combinations is the best as far as anthocyanin content is concerned (average 3.91 mg/g. fr. wt.). Also this amount is attained after 40 days of culture period. But growth Index of the callus growing on this is very low (50.12). In contrast to this hormone combination, 2,4-D (1.0) and Kn (0.25) is better as far as biomass production is concerned. Out of 2,4-D concentration 0.5 and 1.0,1.0 is better in terms of biomass production (GI=221.36). At this concentration anthocyanin content is a bit low (2.767 mg/g fr. wt.) which is less than the amount present in NAA (0.5)+Kn(0.25) containing media. It is evident from this experiment that both IAA and NAA show comparably higher percentage of anthocyanin content per gm fresh weight but the biomass production is very low in both these hormone containing medium. Therefore in subsequent experiments medium containing 2,4-D (1.0 mgl$^{-1}$) and Kn (0.25 mgl$^{-1}$) was used to obtain maximum production index for anthocyanin content. It is very important to mention here that this hormone combination is optimum for ginsenoside production also (0.9–1.2% on Fr. Wt. basis) as earlier reported by us (Pl.Med.65:484–486,1999).

EXAMPLE 2

Different light conditions for callus incubation were tested to study their effect on biomass production and anthocyanin content over a culture span of 90 days. Percent increase in biomass and corresponding anthocyanin content were monitored at 10 days interval and the results are depicted in Table 2. Increase in biomass production was almost similar under 16 hr L-8 hr D (433.172) and continuous light conditions. (414.032), however maximum biomass production reached earlier (50 days) under continuous light condition in comparison to (16 hr L–8 hr D). However under complete darkness through out the culture period, the biomass production reached maximum only upto 50th day i.e. 393.267, (Table 2). As far as anthocyanin production is concerned maximum production was observed under continuous light conditions (2.166 mg/gf. wt.) in comparison to 16 hr. L. and 8 hr.D (1.716 mg./gf. wt). The cultures which were kept continuously in dark produced very little amount of anthocyanin (0.215 mg/g fr. wt) which was 1/10 th of the cultures incubated in continuous light. This indicates clearly that *P sikkimensis* callus cultures produce more anthocyanin in light.

EXAMPLE 3

To characterize the pigment in *P. sikkimensis* callus cultures, freshly harvested callus tissue was extracted with 0.1% HCl—MeOH; concentrated at 40–50° C. and the concentrate was applied directly onto Whatman filter paper No. 3, run in descending order using the solvent system Butanol:Acetic acid:Water: 4:1:5 organic layer at room temperature. The paper was run for 10–15 hrs. The anthocyanin appeared as clear discrete colored bands which are then cut out from the dried papers. These cut bands were eluted with methanol. The eluates are collected and concentrated. The two bands separated on paper in above solvent system having Rf values 0.40 and 0.73, respectively.

TABLE 1

Effect of hormone combination on growth an anthocyanin content of *P. sikkimensis* callus cultures.

| Hormone Treatment | | Culture Period (Days) | | | | |
|---|---|---|---|---|---|---|
| | | 0 | 20 | 40 | 60 | 80 |
| T$_1$ | GI* | 0 | 39.42 | 52.16 | 52.68 | 64.175 |
| | AC** | 1.906 | 2.326 | 2.884 | 1.298 | 0.688 |
| T$_2$ | GI* | 0 | 34.31 | 36.897 | 52.20 | 44.29 |
| | AC** | 1.906 | 2.983 | 2.502 | 1.768 | 0.571 |
| T$_3$ | GI* | 0 | 34.47 | 46.92 | 57.39 | 78.71 |
| | AC** | 1.906 | 2.185 | 2.595 | 1.590 | 0.572 |
| T$_4$ | GI* | 0 | 40.46 | 50.09 | 56.71 | 53.78 |
| | AC** | 1.906 | 2.837 | 3.911 | 1.209 | 0.504 |
| T$_5$ | GI* | 0 | 58.16 | 188.77 | 221.36 | 264.77 |
| | AC** | 1.906 | 0.984 | 2.417 | 2.767 | 0.552 |
| T$_6$ | GI* | 0 | 58.72 | 106.64 | 129.35 | 172.47 |
| | AC** | 1.906 | 1.277 | 2.452 | 3.300 | 0.654 |

*GI = Growth index
**AC = Anthocyanin content (mg/g f.wt.)
T$_1$IAA (1.0 mgl$^{-1}$) + Kn (0.25 mgl$^{-1}$);
T$_2$IAA (0.5 mgl$^{-1}$) + Kn (0.25 mgl$^{-1}$)
T$_3$NAA (1.–0 mgl$^{-1}$) + Kn (0.25 mgl$^{-1}$)+);
T$_4$NAA (0.5 mgl$^{-1}$) + Kn (0.25 mgl$^{-1}$);
T$_5$2,4-D (1.0 mgl$^{-1}$) + Kn (0.25 mgl$^{-1}$) +);
T$_6$2,4-D (0.5 mgl$^{-1}$)+) + Kn (0.25 mgl$^{-1}$)

TABLE 2

Effect of light conditions on growth and anthocyanin content of *P. sikkimensis* callus cultures.

| Culture Duration | Light conditions | | | | | | | |
|---|---|---|---|---|---|---|---|---|
| (days) | 8 hrs. L. 16 hrs. D | | 8 hrs. D. 16 hrs. L. | | 24 hrs. D. | | 24 hrs. L. | |
| | GI | AC | GI | AC | GI | AC | GI | AC |
| 0 | 0 | | 0 | | 0 | 0 | | |
| 7 | 14.221 | 0.258 | 15.424 | 0.214 | 15.589 | 0.286 | 7.886 | 0.285 |
| 14 | 43.684 | 0.283 | 48.295 | 0.197 | 57.895 | 0.263 | 28.959 | 0.240 |
| 21 | 51.292 | 0.142 | 90.608 | 0.313 | 54.829 | 0.187 | 6.069 | 0.097 |
| 28 | 130.481 | 0.230 | 151.835 | 0.372 | 171.605 | 0.288 | 63.128 | 0.907 |
| 35 | 267.935 | 0.165 | 272.717 | 0.468 | 199.278 | 0.093 | 107.883 | 0.697 |
| 42 | 447.765 | 0.264 | 457.333 | 0.727 | 189.32 | 0.128 | 375.758 | 1.632 |
| 49 | 535.00 | 0.068 | 414.815 | 1.686 | 339.08 | 0.102 | 740.659 | 1.147 |

L = Light,
D = Dark;
GI = Growth Index,
AC = Anthocyanin content (mg/g f. wt.)

The Main Advantages of the Present Invention Are

1. The said callus line in this study is capable of producing anthocyanin (within 40–80 days).
2. It has resulted in the generation of a viable option for anthocyanin production along with ginsenoside production.
3. The cultural procedures and condition used for this invention are fully defined and reproducible.
4. The invention provides an efficient means for anthocyanin production along with ginsenosides, that are in high demand in the world market as important health tonics and anti-ageing drug preparations.
5. The anthocyanin rich callus line can be commercially used in candy's, cakes and cold drinks, as it will also contain ginsenosides.

What is claimed is:

1. An anthocyanin producing callus line in cultures of *Panax skikkimensis* said line comprising:
   (a) pink-purple pigmentation,
   (b) growth index in the range of about 221–450 in a culture period in the range of about 50–80 days, preferably in the range of about 40–60 days, and
   (c) having a yield of anthocyanin in the range of about 2–3 mg/gf.wt. from said callus.

2. A method for developing an anthocyanin producing line of *Panax sikkimensis* from root explants wherein the said method comprising the steps of:
   (a) providing an aseptic culture of root explants of *P. sikkimensis* on Medium I to obtain a callus,
   (b) transferring said callus to medium II,
   (c) maintaining and multiplying said callus for over 3 years by regular subculturing in medium II at every 4–6 weeks,
   (d) isolating said anthocyanin producing callus line by selectively subculturing said callus line that exhibit anthocyanin for at least 5 subsequence subcultures, and
   (e) proliferating said callus line by using medium II and incubating said callus line under light conditions.

3. A method of claim 2 wherein said method further comprises cutting said root explants into 4–7 mm pieces; sterilizing said root explants with 1% cetabelon (v/v) for a period of about 5–15 minutes, further sterilizing with 70% (V/v) ethanol for 30 sec., further treating with 0.1% $HgCl_2$ (w/v) for about 1–2 min.

4. A method of claim 2, wherein said medium I is modified Murashige and Skoog's medium supplemented with 200 mg/l myoinositol, 10 mg/l each of thiamine hydrochloride and pyridoxine hydrochloride, and 5 mg/l of nicotinic acid.

5. A method of claim 2 wherein said medium II is obtained by addition of 2,4-dichlorophenoxyacetic acid in the range of about 0.1–2.0 mg/l and Kn in the range of about 0.1–0.5 mg/l.

6. A method of claim 2, wherein said light conditions are 16 hours light, 8 hours dark or 24 hours light for higher anthocyanin production.

7. A method of extracting ginsenosides from *P. sikkimensis* callus line of claim 2, said method comprising the steps of:
   chemically extracting said callus line with 100% methanol four times resulting in a dried extract,
   redissolving said dried extract in water resulting in a solution,
   extracting said solution with n-butanol saturated with water four times,
   collecting the n-butanol fraction for centrifuging and drying under vacuum.

8. The method of claim 7, further comprising extracting an anthocyanin pigment from said callus line by homogenising said callus line in 0.1% (v/v) HCl-methanol resulting in a mixture, filtering said mixture resulting in a supernatant, diluting said supernatant 3 times with HCl-methanol solution, measuring absorbance at wavelengths ranging from 525–535 nm using a spectrophotometer.

9. The method of claim 2 wherein said light conditions are 8 hours dark, 24 hours light and 24 hours dark.

10. The anthocyanin producing callus line of claim 1 having a characteristic DNA profile wherein the lanes 1, 2, 3, 4, 5, 6, 7, 8, 9, 10, 11 and 12 in each gel (upper gel or wild line and lower gel for anthocyanin producing line) represent the PCR amplified fragments produced by the respective template megabase genomic DNA with primers 5' CTG ATG CAT C, 3',5' TGG TCA CTG A 3', 5' AGG GGT CTT G 3',5' GAA ACG GGT G 3',5' AGG GGT CTT G 3', 5' GCG TAA CGC C 3',5' CAG CAC CCA C 3',5' GTT GCG ATC C 3', 5' CAG GCC CTT C 3',5' CGC AGT ACT C 3',5' GTC CTA CTC G 3',5' CTA CAC AGG C 3' and 5' GTC CTT AGC G 3', respectively.

11. The method of claim 2 further comprising adding a hormone combination and concentration of IAA in the range of about 0.5–1.5 mg/l and Kn in the range of about 0.25–0.50 mg/l.

12. The method of claim 2 further comprising adding a hormone combination and concentration of NAA in the range of about 0.5–1.5 mg/l and Kn in the range of about 0.25–0.50 mg/l.

13. The method of claim 2 further comprising adding a hormone combination and concentration of 2,4-dichlorophenoxyacetic acid in the range of about 0.5–1.5 mg/l and Kn in the range of about 0.25–0.50 mg/l.

14. The anthocyanin producing callus line of claim 1 further comprises having ginsenoside.

15. The anthocyanin producing callus line of claim 13, wherein said ginsenoside is used for health tonics and anti-ageing preparations.

16. The anthocyanin producing callus line of claim 1, wherein said anthocyanin is used as a food additive.

\* \* \* \* \*